(12) United States Patent
Uriu

(10) Patent No.: US 11,104,932 B2
(45) Date of Patent: *Aug. 31, 2021

(54) METHOD FOR DETERMINING WHETHER OR NOT ALL OF PYTHIUMS CONTAINED IN TEST SAMPLE ARE NON-PHYTOPATHOGENIC

(71) Applicant: Panasonic Intellectual Property Management Co., Ltd., Osaka (JP)

(72) Inventor: Yoshitsugu Uriu, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/217,466

(22) Filed: Dec. 12, 2018

(65) Prior Publication Data

US 2019/0112631 A1 Apr. 18, 2019

Related U.S. Application Data

(63) Continuation of application No. PCT/JP2016/004419, filed on Sep. 30, 2016.

(30) Foreign Application Priority Data

Aug. 9, 2016 (JP) .............................. JP2016-156199

(51) Int. Cl.
| | | |
|---|---|---|
| *C12Q 1/04* | (2006.01) | |
| *G01N 33/569* | (2006.01) | |
| *C12N 1/14* | (2006.01) | |
| *C12N 1/02* | (2006.01) | |
| *C12R 1/645* | (2006.01) | |

(52) U.S. Cl.
CPC ............... *C12Q 1/04* (2013.01); *C12N 1/02* (2013.01); *C12N 1/14* (2013.01); *C12N 1/145* (2021.05); *G01N 33/56961* (2013.01); *C12R 2001/645* (2021.05)

(58) Field of Classification Search
CPC ........................................................ C12N 1/02
See application file for complete search history.

(56) References Cited

U.S. PATENT DOCUMENTS

| | | | | |
|---|---|---|---|---|
| 7,288,197 B2 * | 10/2007 | Shao | ...................... | C02F 3/085 |
| | | | | 210/615 |
| 2016/0355863 A1 * | 12/2016 | Uriu | ........................ | C12Q 1/04 |
| 2016/0355864 A1 * | 12/2016 | Uriu | ........................ | C12Q 1/04 |

FOREIGN PATENT DOCUMENTS

| | | | | |
|---|---|---|---|---|
| JP | 2005-287337 | 10/2005 | | |
| WO | WO-2011090802 A1 * | 7/2011 | ............... | C12Q 1/04 |

OTHER PUBLICATIONS

Diez-Navajas et al., Micron, 2007, 38:680-683.*
International Search Report of PCT application No. PCT/JP2016/004419 dated Jan. 10, 2017.
Paul F. Morris et al., "Chemotropic and Contact Responses of Phytophthora sojae Hyphae to Soybean Isoflavonoids and Artificial Substrates", Plant Physiol. (1998) 117: 1171-1178.
Akira Matsuura et al., "Occurrence of damping-off of sweet pea (*Lathyrus odoratus* L) caused by Pythium aphanidermatum (Edson) Fitzpatrick and Pythium myriotylum Drechsler", Kyushu Pl. Prot. Res. vol. 49, (2003), pp. 66-70.
Kanak Bala et al., "*Pythium rhizo-oryzae* sp. nov. Isolated from Paddy Fields: Taxonomy, ITS Region of rDNA, and Comparison with Related Species", Current Microbiology vol. 52 (2006), pp. 102-107.

* cited by examiner

*Primary Examiner* — Bin Shen

(74) *Attorney, Agent, or Firm* — McDermott Will & Emery LLP

(57) ABSTRACT

The present invention provides a method for determining whether or not all of pythiums contained in a test sample are non-phytopathogenic. The method comprises: (a) putting the test sample on a front surface of a film comprising a through-hole having a cross-sectional area of not less than 0.785 square micrometers and not more than 7.065 square micrometers; (b) leaving the test sample at rest after the step (a); (c) observing a back surface of the film after the step (b); and (d) determining that all of the pythiums contained in the test sample are non-phytopathogenic, if pseudohyphae are not found on the back surface of the film in the step (c).

19 Claims, 9 Drawing Sheets

US 11,104,932 B2

METHOD FOR DETERMINING WHETHER OR NOT ALL OF PYTHIUMS CONTAINED IN TEST SAMPLE ARE NON-PHYTOPATHOGENIC

BACKGROUND

1. Technical Field

The present invention relates to a method for determining whether or not all of pythiums contained in a test sample are non-phytopathogenic.

2. Description of the Related Art

Patent Literature 1 discloses a method for counting the number of mold cells. FIG. 14 shows a cross-sectional view of a microporous membrane supporting material which is used for the method disclosed in Patent Literature 1. The method for counting the number of mold cells disclosed in Patent Literature 1 provides a method for counting the number of mold cells in a specimen by the culture for a short time and capable of accurately counting the cell number. In the method for counting the number of mold cells disclosed in Patent Literature 1, the extended multiple pseudomycelia of a mold cell 13 cultured by a liquid culture or a mold cell 13 cultured on a microporous membrane 1 of a microporous membrane supporting material 4 are photographed 5 and the shape, area and luminous intensity are recognized and analyzed by an image analytic means 10. The number of the mold cells 13 can be counted by the culture for a short time. The microporous membrane 1 is interposed between a pressing ring 2 and a base 3.

Non-patent Literature 1 discloses that pseudohyphae of Phytophthora sojae, which is one kind of phytopathogenic pythiums, penetrate a PET film having pores each having a dimeter of 3 micrometers.

CITATION LIST

Patent Literature

Patent Literature 1: Japanese Patent Application laid-open Publication No. 2005-287337A

Non-Patent Literature

Non-patent Literature 1: Paul F. Morris. et. al. "Chemotropic and Contact Responses of Phytophthora sojae Hyphae to Soybean Isoflavonoids and Artificial Substrates", Plant Physiol. (1998) 117: 1171-1178

SUMMARY

An object of the present invention is to provide a method for determining whether or not all of pythiums contained in a test sample are non-phytopathogenic.

The present invention provides a method for determining whether or not all of pythiums contained in a test sample are non-phytopathogenic, the method comprising:
  (a) putting the test sample on a front surface of a film comprising a through-hole having a cross-sectional area of not less than 0.785 square micrometers and not more than 7.065 square micrometers;
  (b) leaving the test sample at rest after the step (a);
  (c) observing a back surface of the film after the step (b); and
  (d) determining that all of the pythiums contained in the test sample are non-phytopathogenic, if pseudohyphae are not found on the back surface of the film in the step (c).

The present invention provides a method for determining whether or not all of pythiums contained in a test sample are non-phytopathogenic.

DETAILED DESCRIPTION OF THE EMBODIMENT

First, pythiums will be described. Pythiums are roughly divided into a phytopathogenic pythium and a non-phytopathogenic pythium. An example of the phytopathogenic pythium is Pythium helicoides, Pythium myliotaerum, or Pythium aphanidermatum. These phytopathogenic pythiums cause pythium red blight and a root rot disease. First, these phytopathogenic pythiums infect a root of a plant. Then, these phytopathogenic pythiums cause the root of the plant to rot. Finally, these phytopathogenic Pythiums kill the plant. An example of the non-phytopathogenic pythium is Pythium dissotocum, Pythium catenulatum, Pythium torulosum, or Pythium inflatum. Pythium dissotocum may be classified as a weak-phytopathogenic pythium. In the instant specification, the weak-phytopathogenic pythium is classified as a non-phytopathogenic pythium. In other words, the word "non-phytopathogenic pythium" includes a weak-phytopathogenic pythium. The word "phytopathogenic pythium" does not include a weak-phytopathogenic pythium.

The term "phytopathogenic" means to have pathogenicity to plants. The term "non-phytopathogenic" means not to have pathogenicity to plants. Even if a pythium has pathogenicity, however, if the pythium has no pathogenicity to plants, the pythium is non-phytopathogenic. In other words, if a pythium does not have adverse effects on plants, the pythium is non-phytopathogenic. The prefix "non-" included in the term "non-phytopathogenic" does not modify "phyto". The prefix "non-" modifies "pathogenic".

Hereinafter, the embodiment of the present invention will be described in more detail with reference to the drawings.

(Step (a))

In the step (a), a test sample is put on a front surface of a film comprising a through-hole having a cross-sectional area of not less than 0.785 square micrometers and not more than 7.065 square micrometers.

Figure 1:
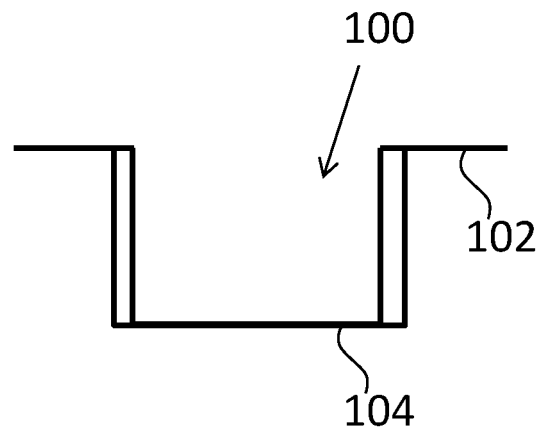
FIG. 1 shows a cross-sectional view of a container.

In particular, as shown in FIG. 1, a container 100 is prepared. It is desirable that the container 100 comprises a flange 102 at the upper end thereof. The bottom surface of the container 100 is formed of a film 104. An example of the material of the film 104 is organic resin such as polyethylene terephthalate.

Figure 2:
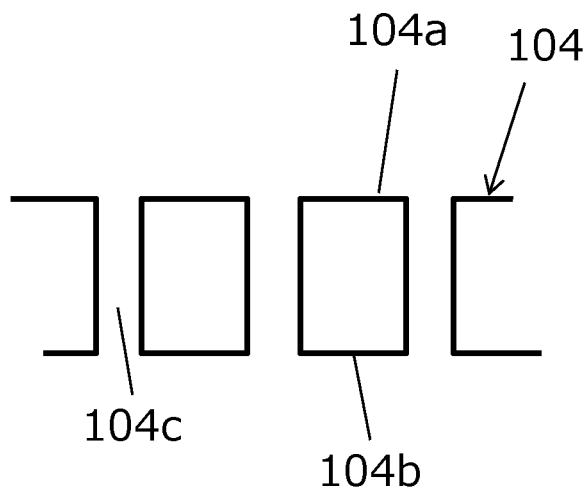
FIG. 2 shows a cross-sectional view of a film.

FIG. 2 shows a cross-sectional view of the film 104. The film 104 has a front surface 104a, a back surface 104b, and a through-hole 104c. One of the characteristics of the present invention is a cross-sectional area of the through-hole 104c.

The through-hole 104c has a cross-sectional area of not less than 0.785 square micrometers and not more than 7.065 square micrometers. In particular, it is desirable that the through-hole 104c has a shape of a cylinder having a diameter of not less than 1 micrometer and not more than 3 micrometers. The importance of these cross-sectional area and diameter will be described later.

Figure 3:
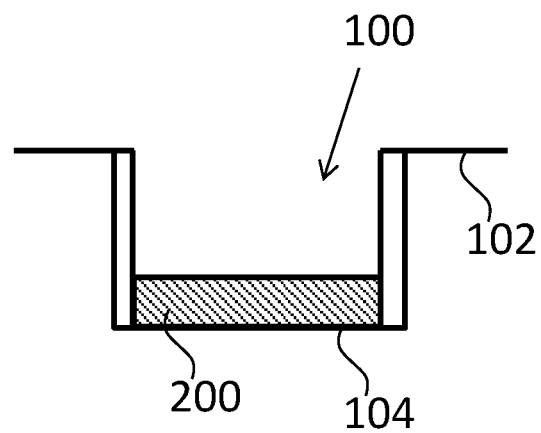
FIG. 3 shows a cross-sectional view of the container to which a test sample has been supplied.
Figure 4:
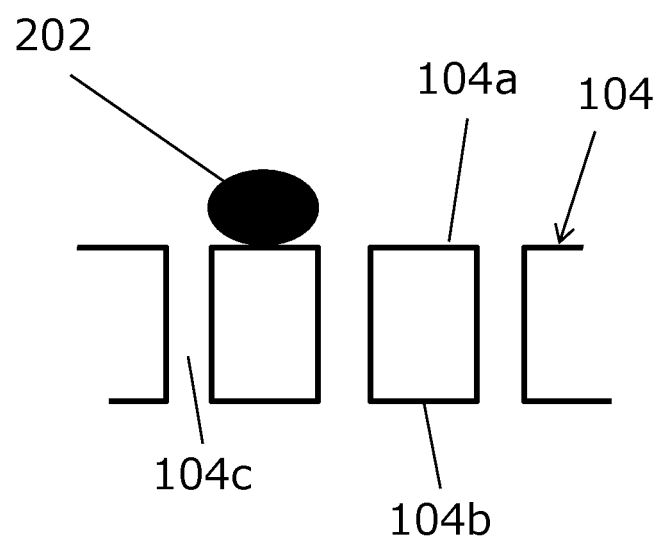
FIG. 4 shows a cross-sectional view of the film having a front surface on which a phytopathogenic pythium has been put.
Figure 5:
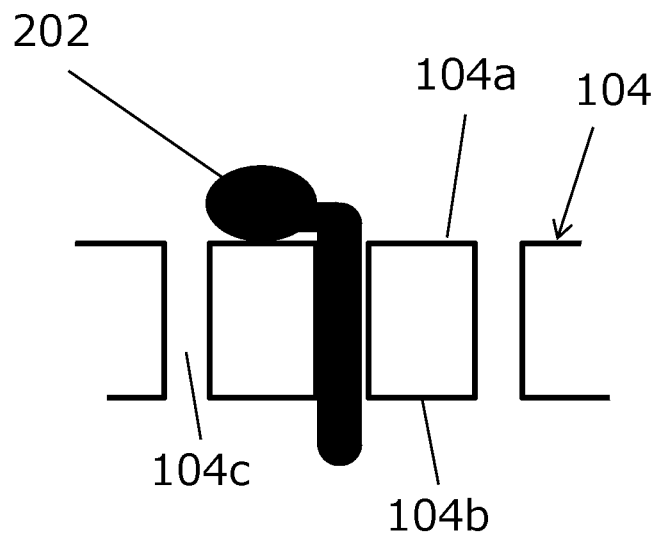
FIG. 5 is a cross-sectional view showing how the phytopathogenic pythium penetrates the film.

As shown in FIG. 3, a test sample 200 is supplied to the inside of this container 100. In this way, the test sample 200 is put on the front surface 104a of the film 104. In the present embodiment, the test sample 200 contains at least one kind of pythiums. Therefore, as shown in FIG. 4, a pythium 202 is disposed on the front surface 104a of the film 104.

The test sample 200 is solid, liquid, or gaseous. It is desirable that the test sample 200 is solid or liquid. An example of the solid test sample 200 is soil or a crushed plant. Another example is an agricultural material such as vermiculite, rock wool or urethane. An example of the liquid test sample 200 is agricultural water, a solution used for hydroponic culture, a liquid used to wash a plant, a liquid extracted from a plant, a liquid used to wash an agricultural material, or a liquid used to wash clothing or shoes of a worker.

(Step (b))

In the step (b), the test sample 200 is left at rest for a certain time after the step (a). The importance of the cross-sectional area or the diameter of the through-hole 104*c* will be described below.

In the step (b), various pythiums contained in the test sample 200 are grown. When the through-hole 104*c* has a cross-sectional area of not less than 0.785 square micrometers and not more than 7.065 square micrometers, as shown in FIG. 5, the phytopathogenic pythium 202 grows up so as to penetrate the through-hole 104*c*. This is demonstrated in the inventive examples and the comparative examples which will be described later. As a result, pseudohyphae of the phytopathogenic pythium 202 appear on the back surface 104*b* of the film 104. On the other hand, within this range of the cross-sectional area, the non-phytopathogenic pythium does not penetrate the through-hole 104*c*. For this reason, the non-phytopathogenic pythium does not appear on the back surface 104*b* of the film 104. In this way, the phytopathogenic pythium 202 appears on the back surface 104*b* selectively. In other words, the phytopathogenic pythium 202 appears outside of the container 100 selectively.

When the through-hole 104*c* has a cross-sectional area less than 0.785 square micrometers, neither the non-phytopathogenic pythium nor the phytopathogenic pythium penetrates the through-hole 104*c*. On the other hand, when the through-hole 104*c* has a cross-sectional area more than 7.065 square micrometers, not only the phytopathogenic pythium but also the non-phytopathogenic pythium penetrate the through-hole 104*c*. For this reason, the selectivity is lost when the through-hole 104*c* has a cross-sectional area less than 0.785 square micrometers or more than 7.065 square micrometers.

The thickness of the film 104 is not limited, as far as the phytopathogenic pythium 202 appears outside of the container 100 selectively. The film 104 may have a thickness of not less than 10 micrometers and not more than 100 micrometers. It is desirable that the film 104 has plural through-holes 104*c*, as shown in FIG. 3-FIG. 5.

A culture medium may be supplied to the test sample 200 to accelerate the incubation of the pythiums. In particular, a culture medium may be supplied to the inside of the container 100 containing the test sample 200. It is desirable that the culture medium is liquid. The culture medium may be supplied in the step (b). Alternatively, the culture medium may be supplied prior to the step (b). In other words, the culture medium may be supplied in the step (a). The culture medium may be supplied to the inside of the container 100 prior to the step (a).

FIG. 6 shows another method for accelerating the incubation of the pythiums. As shown in FIG. 6, it is desirable that the back surface 104*b* of the film 104 is in contact with a liquid culture medium 302. First, a second container 300 having the liquid culture medium 302 therein is prepared. Hereinafter, the container 100 is referred to as "first container 100" to distinguish it from the second container 300. The first container 100 is stacked on the second container 300 in such a manner that the lower surface of the flange 102 is in contact with the upper end of the second container 300. In other words, the first container 100 is supported by the upper end of the second container 300. In this way, the liquid culture medium 302 is sandwiched between the back surface 104*b* of the film 104 and the bottom surface of the second container 300.

Alternatively, after the first container 100 is stacked on the second container 300, the liquid culture medium 302 may be supplied between the back surface 104*b* of the film 104 and the bottom surface of the second container 300.

Since the liquid culture medium 302 is in contact with the back surface 104*b* of the film 104, the liquid culture medium 302 is soaked up by a capillary phenomenon through the through-hole 104*c*. In place of the liquid culture medium 302, a viscous solid culture medium may also be used. In this case, when the first container 100 is stacked on the second container 300, the viscous solid culture medium is transformed so as to penetrate the through-hole 104*c*. In this way, the culture medium 302 reaches the inside of the container 100. By the culture medium 302 which has reached the inside of the container 100, the incubation of the pythiums is accelerated. As shown in FIG. 6, both of a solid culture medium 304 and the liquid culture medium 302 may be used. In this case, the liquid culture medium 302 is sandwiched between the solid culture medium 304 and the film 104.

(Step (c))

In the step (c), the back surface 104*b* of the film 104 is observed after the step (b). It is desirable that the back surface 104*b* is observed using an optical microscope.

The phytopathogenic pythium 202 appears on the back surface 104b of the film 104, as described in the step (b). On the other hand, the non-phytopathogenic pythium does not appear on the back surface 104b of the film 104. In this way, in the present invention, the phytopathogenic pythium 202 appears on the back surface 104b of the film 104 selectively.

In other words, the phytopathogenic pythium 202 penetrates the through-hole 104c, whereas the non-phytopathogenic pythium does not penetrate the through-hole 104c. For this reason, the non-phytopathogenic pythium does not appear on the back surface 104b of the film 104. In this way, the phytopathogenic pythium 202 appears on the back surface 104b selectively. In other words, the phytopathogenic pythium 202 appears outside of the container 100 selectively.

In the step (c), it is observed whether or not the phytopathogenic pythium 202 appears on the back surface 104b of the film 104.

In particular, whether or not the phytopathogenic pythium 202 appears on the back surface 104b of the film 104 is observed as below.

First, the test sample 200 is turned into a gel. In more detail, an agarose aqueous solution is supplied to the first container 100. Then, the agarose aqueous solution containing the test sample 200 is stirred. Finally, the test sample 200 is left at rest at room temperature. In this way, the test sample is turned into a gel.

Then, the first container 100 is drawn up from the second container 300. Prior to the gelation, the first container 100 may be drawn up from the second container 300.

Figure 7:
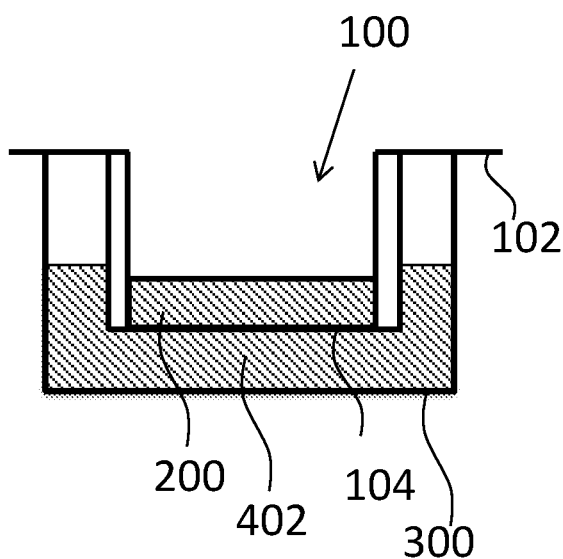
FIG. 7 shows a cross-sectional view, subsequently to FIG. 6, of one example of a method for accelerating the incubation of the pythium.

The liquid culture medium 302 and the solid culture medium 304 are removed from the second container 300. Then, a fluorescent agent having oomycete combining ability is added to the inside of the second container 300. Hereinafter, such a fluorescent agent is referred to as "oomycete fluorescent agent". The reference number of the oomycete fluorescent agent is 402. Then, as shown in FIG. 7, the first container 100 is stacked on the second container 300 having the oomycete fluorescent agent 402 therein. Alternatively, the oomycete fluorescent agent 402 may be supplied between the back surface 104b of the film 104 and the bottom surface of the second container 300 after the first container 100 is stacked on the second container 300.

A part of the phytopathogenic pythium 202 which has appeared on the back surface 104b of the film 104 is dyed with the oomycete fluorescent agent 402. Since the test sample 200 has been turned into a gel, the oomycete fluorescent agent 402 does not spread into the first container 100. For this reason, the non-phytopathogenic pythium contained in the first container 100 is not dyed with the oomycete fluorescent agent 402.

Figure 8:
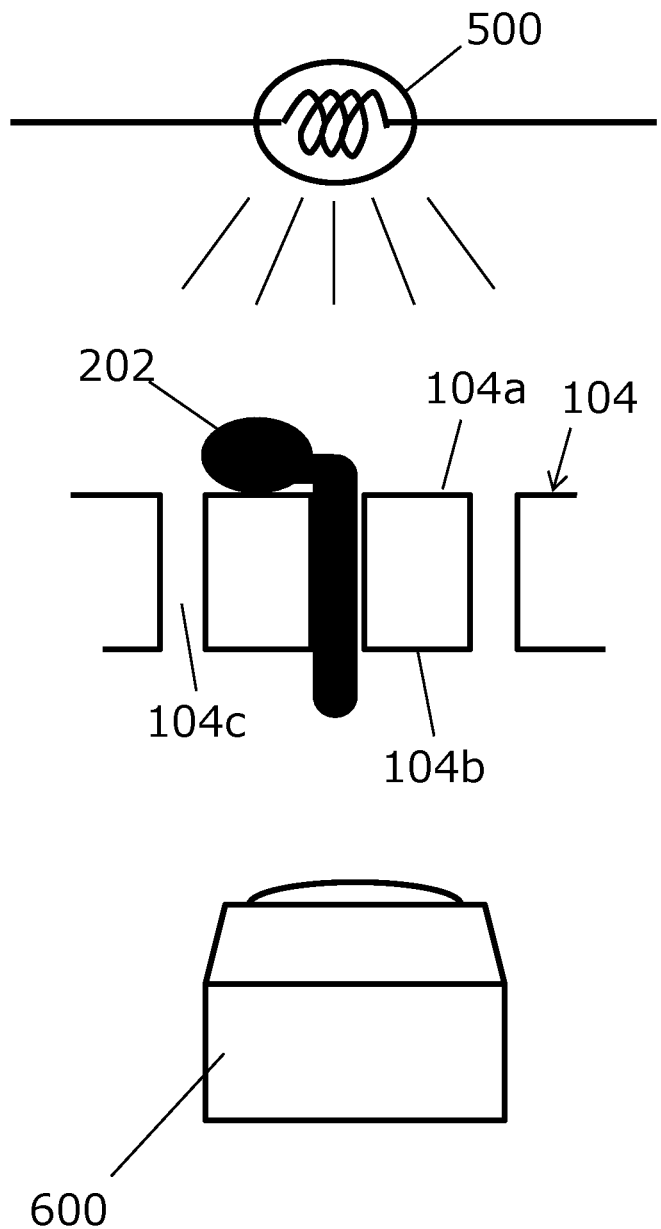
FIG. 8 is a cross-sectional view showing how to observe the pythium from the back surface of the film.

As shown in FIG. 8, the thus-dyed phytopathogenic pythium 202 is observed using a microscope 600 located under the back surface 104b of the film 104, while the film 104 is irradiated with light using a light source 500 located over the front surface 104a of the film 104.

Figure 9:
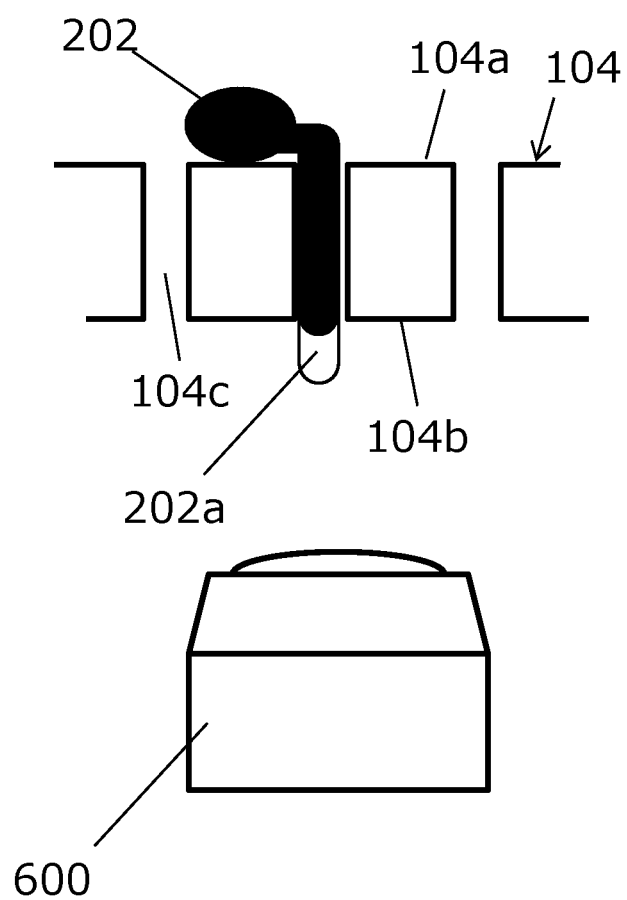
FIG. 9 is a cross-sectional view showing how to observe the pythium from the back surface of the film.

In place of the oomycete fluorescent agent 402, a fluorescent agent having pythium combining ability may also be used. In this case, a part 202a of the phytopathogenic pythium 202 which has appeared on the back surface 104b of the film 104 is dyed with the fluorescent agent having pythium combining ability. As shown in FIG. 9, the phytopathogenic pythium 202 dyed with the fluorescent agent having pythium combining ability is observed using the microscope 600 located under the back surface 104b of the film 104.

(Step (d))

In the step (d), it is determined that all of the pythiums contained in the test sample 200 are non-phytopathogenic, if pseudohyphae of the pythiums are not found on the back surface 104b of the film 104 in the step (c). Needless to say, it is determined that all of the pythiums contained in the test solution 200 are not necessarily non-phytopathogenic, if the pythiums are found on the back surface 104b of the film 104 in the step (c).

EXAMPLES

The present invention will be described in more detail with reference to the following examples.

(Incubation of Pythium Torulosum)

Pythium torulosum, one of non-phytopathogenic pythiums, was inoculated on a cornmeal agar culture medium together with dried turfgrass. Then, the culture medium was left at rest at a temperature of 25 degrees Celsius for 24 hours. Pythium torulosum was given by Professor Kageyama, who belongs to Gifu University River Basin Research Center. The dried turfgrass was provided by drying Korean lawn grass sterilized in accordance with a high temperature and high pressure sterilization method at 60 degrees Celsius for approximately 24 hours.

Then, the dried turfgrass to which a pseudohypha adhered was picked up from the culture medium. The thus-picked dried turfgrass was provided afloat to the pure water contained in a petri dish. The volume of the pure water was 20 milliliters.

After 18 hours, the water contained in the petri dish was observed using an optical microscope. As a result, the present inventor confirmed that zoospores of Pythium torulosum were released in the water contained in the petri dish. In this way, an aqueous solution containing Pythium torulosum was provided. Hereinafter, this aqueous solution is referred to as "non-phytopathogenic aqueous solution".

(Preparation of Culture Medium)

A potato dextrose agar culture medium melted at a high temperature was added to the second container 300. The potato dextrose agar culture medium had a volume of 250 microliters. Then, the potato dextrose agar culture medium was turned into a gel at room temperature. In this way, the potato dextrose agar culture medium gel was provided as the solid culture medium 304.

A hydroponic culture solution (e.g., Otsuka-SA nutrient solution) having a volume of 350 microliters was added as the liquid culture medium 302 to the second container 300 containing the potato dextrose agar culture medium gel. In this way, the second container 300 containing the liquid culture medium 302 and the solid culture medium 304 was prepared.

Inventive Example 1A

The first container 100 shown in FIG. 1 was prepared. This first container 100 was made of plastic. As shown in FIG. 2, the bottom surface of the first container 100 was formed of a polyethylene terephthalate film 104 (available from Merck KGaA, trade name: Millicell (registered trademark) PISP 12R 48). This polyethylene terephthalate film 104 comprised plural through-holes 104c each having a diameter of 3 micrometers. The plural through-holes 104c were provided randomly in the film 104. According to Merck KGaA, the diameter of the through-hole 104c may have a margin of error of approximately ± 10%.

Figure 6:
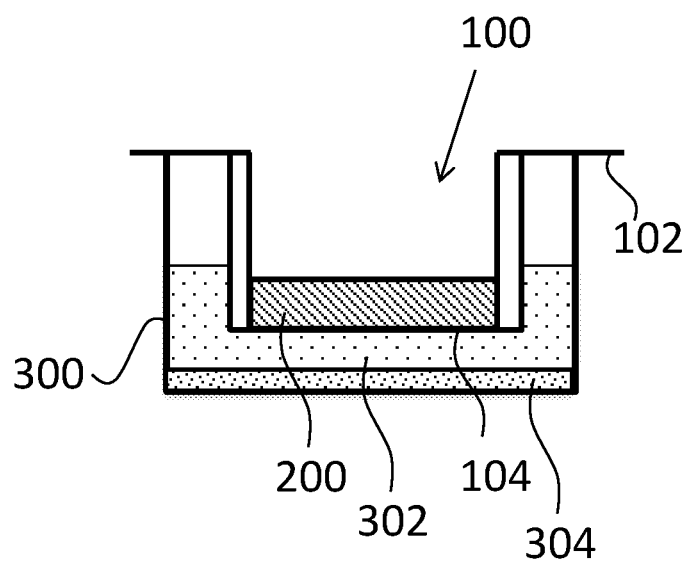
FIG. 6 shows a cross-sectional view of one example of a method for accelerating the incubation of the pythium.

Then, as shown in FIG. 6, the first container 100 was stacked on the second container 300. The back surface 104b of the film 104 was in contact with the liquid culture medium 302. Subsequently, the hydroponic culture solution having a volume of 200 microliters was added to the inside of the first container 100. Furthermore, the non-phytopathogenic aqueous solution containing 200 zoospores of Pythium torulosum was added to the inside of the first container 100.

The first container 100 was left at rest at a temperature of 25 degrees Celsius for 6 hours.

Subsequently, the first container 100 was separated from the second container 300. The non-phytopathogenic aqueous solution contained in the first container 100 was removed. Then, an agarose aqueous solution having a concentration of 2% was added to the inside of the first container 100. The agarose aqueous solution was turned into a gel at room temperature.

A fluorescent agent having oomycete combining ability (available from Beckton Dickinson and Company, trade name: Calcofluor White (BD261195)) having a volume of 600 milliliters was added to the inside of the second container 300. The final concentration of the fluorescent agent having oomycete combining ability was 0.005%.

Then, the first container 100 was stacked on the second container 300 again. The back surface 104b of the film 104 was in contact with the fluorescent agent having oomycete combining ability. The first container 100 was left at rest at 25 degrees Celsius for 10 minutes. Since the gel was located in the first container 100, the fluorescent agent having oomycete combining ability did not spread into the first container 100.

Subsequently, the first container 100 was separated from the second container 300. The fluorescent agent having oomycete combining ability contained in the second container 300 was removed. Then, a buffer solution was added to the inside of the second container 300. The following Table 1 shows components contained in this buffer solution and their concentrations.

TABLE 1

| Component | Concentration (mmol/L) |
| --- | --- |
| NaCl | 137 |
| KCl | 2.7 |
| $Na_2HPO_4$ | 10 |
| $KH_2PO_4$ | 1.76 |

As shown in FIG. 9, the back surface 104b of the film 104 was observed using a fluorescent microscope 600 (available from Molecular Devices Japan K.K. Trade name: ImageXpress MICRO). Table 2 shows filters and a lens used for the fluorescent microscope 600.

TABLE 2

| | |
| --- | --- |
| Excitation filter | Band pass filter having a center wavelength of 377 nanometers and a band width of 11 nanometers |
| Fluorescence filter | Band pass filter having a center wavelength of 447 nanometers and a band width of 60 nanometers |
| Object lens | Magnification: 10 times/Numerical aperture: 0.30 |

Figure 10:
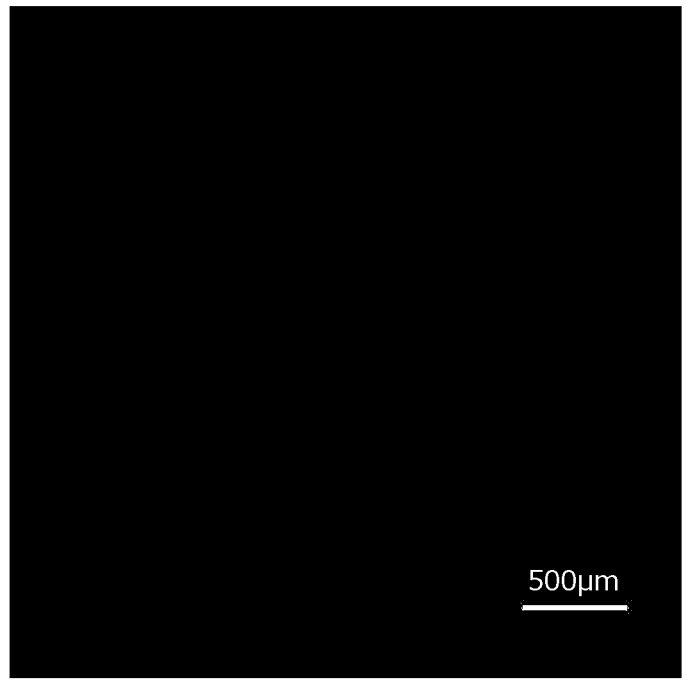
FIG. 10 is a microscope photograph of the back surface of the film in the inventive example 1A.

FIG. 10 is a microscope photograph of the back surface 104b of the film 104 in the inventive example 1A. As seen in FIG. 10, pseudohyphae of Pythium torulosum do not appear on the back surface 104b. This means that the pseudohyphae of Pythium torulosum did not penetrate the through-holes 104c.

Inventive Example 1B

In the inventive example 1B, an experiment similar to the inventive example 1A was conducted, except that each of the through-holes 104c had a diameter of 1 micrometer. In particular, a polyethylene terephthalate film 104 (available from Merck KGaA, trade name: Millicell PIRP 12R 48) was used.

Figure 11:
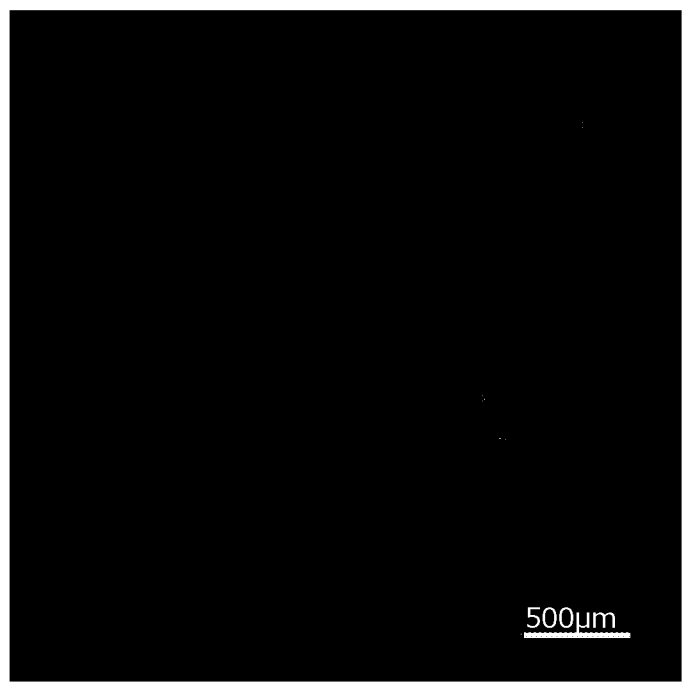
FIG. 11 is a microscope photograph of the back surface of the film in the inventive example 1 B.

FIG. 11 is a microscope photograph of the back surface 104b of the film 104 in the inventive example 1B. As seen in FIG. 11, pseudohyphae of Pythium torulosum do not appear on the back surface 104b. This means that the pseudohyphae of Pythium torulosum did not penetrate the through-holes 104c.

Comparative Example 1C

In the comparative example 1C, an experiment similar to the inventive example 1A was conducted, except that each of the through-holes 104c had a diameter of 0.4 micrometers. In particular, a polyethylene terephthalate film 104 (available from Merck KGaA, trade name: Millicell PIHT 12R 48) was used.

Figure 12:
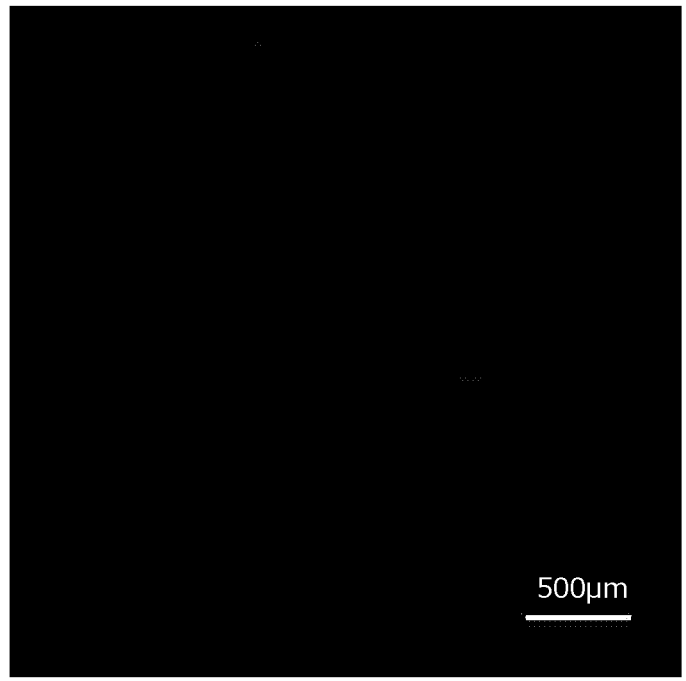
FIG. 12 is a microscope photograph of the back surface of the film in the comparative example 1C.

FIG. 12 is a microscope photograph of the back surface 104b of the film 104 in the comparative example 1C. As seen in FIG. 12, pseudohyphae of Pythium torulosum do not appear on the back surface 104b. This means that the pseudohyphae of Pythium torulosum did not penetrate the through-holes 104c.

Comparative Example 1D)

In the comparative example 1D, an experiment similar to the inventive example 1A was conducted, except that each of the through-holes 104c had a diameter of 5 micrometers. In particular, a polyethylene terephthalate film 104 (available from Merck KGaA, trade name: Millicell PIMP 12R 48) was used.

Figure 13:
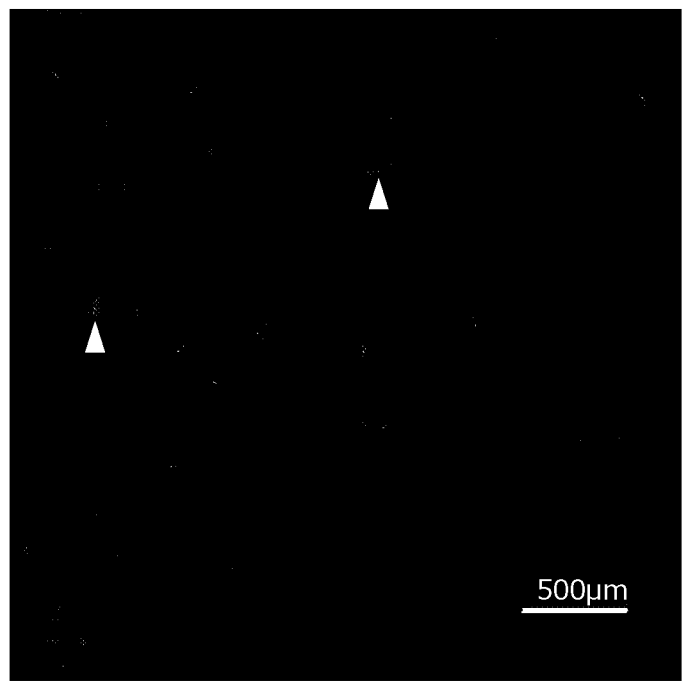
FIG. 13 is a microscope photograph of the back surface of the film in the comparative example 1D.
Figure 14:
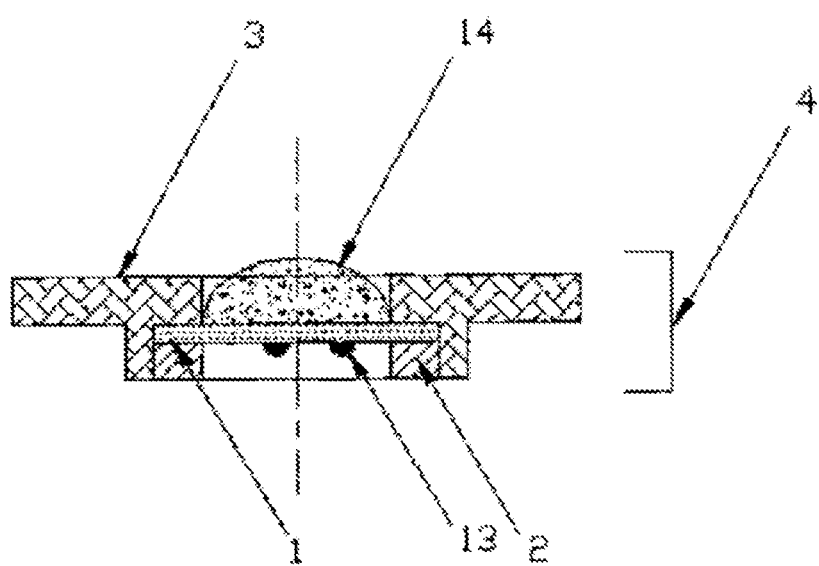
FIG. 14 shows a cross-sectional view of the microporous membrane supporting material used for the method for counting the number of mold cells disclosed in Patent Literature 1.

FIG. 13 is a microscope photograph of the back surface 104b of the film 104 in the comparative example 1D. As seen in FIG. 13, pseudohyphae of Pythium torulosum appear on the back surface 104b. This means that the pseudohyphae of Pythium torulosum penetrated the through-hole 104c.

Comparative Example 1E)

In the comparative example 1E, an experiment similar to the Inventive example 1A was conducted, except that each of the through-holes 104c had a diameter of 8 micrometers. In particular, a polyethylene terephthalate film 104 (available from Merck KGaA, trade name: Millicell PIEP 12R 48) was used.

Inventive Example 2

In the inventive examples 2A-2B and the comparative examples 2C-2E, a non-phytopathogenic aqueous solution containing zoospores of Pythium catenulatum was used in place of the non-phytopathogenic aqueous solution containing zoospores of Pythium torulosum. Similarly to Pythium torulosum, Pythium catenulatum is also one kind of non-phytopathogenic pythiums. A non-phytopathogenic aqueous solution containing zoospores of Pythium catenulatum was prepared similarly to the case of the non-phytopathogenic aqueous solution containing zoospores of Pythium torulosum.

Inventive Example 2A

In the inventive example 2A, an experiment similar to the inventive example 1A was conducted, except that the aqueous solution contained not Pythium torulosum but Pythium catenulatum. Each of the through-holes 104c had a diameter of 3 micrometers.

Inventive Example 2B

In the inventive example 2B, an experiment similar to the inventive example 1B was conducted, except that the aqueous solution contained not Pythium torulosum but Pythium catenulatum. Each of the through-holes 104c had a diameter of 1 micrometer.

Comparative Example 2C

In the comparative example 2C, an experiment similar to the comparative example 1C was conducted, except that the aqueous solution contained not Pythium torulosum but Pythium catenulatum. Each of the through-holes 104c had a diameter of 0.4 micrometers.

Comparative Example 2D

In the comparative example 2D, an experiment similar to the comparative example 1D was conducted, except that the aqueous solution contained not Pythium torulosum but Pythium catenulatum. Each of the through-holes 104c had a diameter of 5 micrometers.

Comparative Example 2E

In the comparative example 2E, an experiment similar to the comparative example 1E was conducted, except that the aqueous solution contained not Pythium torulosum but Pythium catenulatum. Each of the through-holes 104c had a diameter of 8 micrometers.

Inventive Example 3

In the inventive examples 3A-3B and the comparative examples 3C-3E, a non-phytopathogenic aqueous solution containing zoospores of Pythium inflatum was used in place of the non-phytopathogenic aqueous solution containing zoospores of Pythium torulosum. Similarly to Pythium torulosum, Pythium inflatum is also one kind of non-phytopathogenic pythiums. A non-phytopathogenic aqueous solution containing zoospores of Pythium inflatum was prepared similarly to the case of the non-phytopathogenic aqueous solution containing zoospores of Pythium torulosum.

Inventive Example 3A

In the inventive example 3A, an experiment similar to the inventive example 1A was conducted, except that the aqueous solution contained not Pythium torulosum but Pythium inflatum. Each of the through-holes 104c had a diameter of 3 micrometers.

Inventive Example 3B

In the inventive example 3B, an experiment similar to the inventive example 1B was conducted, except that the aqueous solution contained not Pythium torulosum but Pythium inflatum. Each of the through-holes 104c had a diameter of 1 micrometer.

Comparative Example 3C

In the comparative example 3C, an experiment similar to the comparative example 1C was conducted, except that the aqueous solution contained not Pythium torulosum but Pythium inflatum. Each of the through-holes 104c had a diameter of 0.4 micrometers.

Comparative Example 3D

In the comparative example 3D, an experiment similar to the comparative example 1D was conducted, except that the aqueous solution contained not Pythium torulosum but Pythium inflatum. Each of the through-holes 104c had a diameter of 5 micrometers.

Comparative Example 3E

In the comparative example 3E, an experiment similar to the comparative example 1E was conducted, except that the aqueous solution contained not Pythium torulosum but Pythium inflatum. Each of the through-holes 104c had a diameter of 8 micrometers.

Comparative Example 4

In the comparative examples 4A-4E, a phytopathogenic aqueous solution containing zoospores of Pythium helicoides was used in place of the non-phytopathogenic aqueous solution containing zoospores of Pythium torulosum. Unlike Pythium torulosum, Pythium helicoides is one kind of phytopathogenic pythiums. A phytopathogenic aqueous solution containing zoospores of Pythium helicoides was prepared similarly to the case of the non-phytopathogenic aqueous solution containing zoospores of Pythium torulosum.

Comparative Example 4A

In the comparative example 4A, an experiment similar to the inventive example 1A was conducted, except that the aqueous solution contained not Pythium torulosum but Pythium helicoides. Each of the through-holes 104c had a diameter of 3 micrometers.

Comparative Example 4B

In the comparative example 4B, an experiment similar to the inventive example 1B was conducted, except that the aqueous solution contained not Pythium torulosum but Pythium helicoides. Each of the through-holes 104c had a diameter of 1 micrometer.

Comparative Example 4C

In the comparative example 4C, an experiment similar to the comparative example 1C was conducted, except that the aqueous solution contained not Pythium torulosum but Pythium helicoides. Each of the through-holes 104c had a diameter of 0.4 micrometers.

Comparative Example 4D

In the comparative example 4D, an experiment similar to the comparative example 1D was conducted, except that the aqueous solution contained not Pythium torulosum but Pythium helicoides. Each of the through-holes 104c had a diameter of 5 micrometers.

Comparative Example 4E

In the comparative example 4E, an experiment similar to the comparative example 1E was conducted, except that the aqueous solution contained not Pythium torulosum but Pythium helicoides. Each of the through-holes 104c had a diameter of 8 micrometers.

Comparative Example 5

In the comparative examples 5A-5E, a phytopathogenic aqueous solution containing zoospores of Pythium myliotaerum was used in place of the non-phytopathogenic aqueous solution containing zoospores of Pythium torulosum. Unlike Pythium torulosum, Pythium myliotaerum is one kind of phytopathogenic pythiums. A phytopathogenic aqueous solution containing zoospores of Pythium myliotaerum was prepared similarly to the case of the non-phytopathogenic aqueous solution containing zoospores of Pythium torulosum.

Comparative example 5A

In the comparative example 5A, an experiment similar to the inventive example 1A was conducted, except that the aqueous solution contained not Pythium torulosum but Pythium myliotaerum. Each of the through-holes 104c had a diameter of 3 micrometers.

Comparative Example 5B

In the comparative example 5B, an experiment similar to the inventive example 1B was conducted, except that the aqueous solution contained not Pythium torulosum but Pythium myliotaerum. Each of the through-holes 104c had a diameter of 1 micrometer.

Comparative Example 5C

In the comparative example 5C, an experiment similar to the comparative example 1C was conducted, except that the aqueous solution contained not Pythium torulosum but Pythium myliotaerum. Each of the through-holes 104c had a diameter of 0.4 micrometers.

Comparative Example 5D

In the comparative example 5D, an experiment similar to the comparative example 1D was conducted, except that the aqueous solution contained not Pythium torulosum but Pythium myliotaerum. Each of the through-holes 104c had a diameter of 5 micrometers.

Comparative Example 5E

In the comparative example 5E, an experiment similar to the comparative example 1E was conducted, except that the aqueous solution contained not Pythium torulosum but Pythium myliotaerum. Each of the through-holes 104c had a diameter of 8 micrometers.

Comparative Example 6

In the comparative examples 6A-6E, a phytopathogenic aqueous solution containing zoospores of Pythium aphanidermatum was used in place of the non-phytopathogenic aqueous solution containing zoospores of Pythium torulosum. Unlike Pythium torulosum, Pythium aphanidermatum is one kind of phytopathogenic pythiums. A phytopathogenic aqueous solution containing zoospores of Pythium aphanidermatum was prepared similarly to the case of the non-phytopathogenic aqueous solution containing zoospores of Pythium torulosum.

Comparative example 6A

In the comparative example 6A, an experiment similar to the inventive example 1A was conducted, except that the aqueous solution contained not Pythium torulosum but Pythium aphanidermatum. Each of the through-holes 104c had a diameter of 3 micrometers.

Comparative Example 6B

In the comparative example 6B, an experiment similar to the inventive example 1B was conducted, except that the aqueous solution contained not Pythium torulosum but Pythium aphanidermatum. Each of the through-holes 104c had a diameter of 1 micrometer.

Comparative Example 6C

In the comparative example 6C, an experiment similar to the comparative example 1C was conducted, except that the aqueous solution contained not Pythium torulosum but Pythium aphanidermatum. Each of the through-holes 104c had a diameter of 0.4 micrometers.

Comparative Example 6D

In the comparative example 6D, an experiment similar to the comparative example 1D was conducted, except that the aqueous solution contained not Pythium torulosum but Pythium aphanidermatum. Each of the through-holes 104c had a diameter of 5 micrometers.

Comparative Example 6E

In the comparative example 6E, an experiment similar to the comparative example 1E was conducted, except that the aqueous solution contained not Pythium torulosum but Pythium aphanidermatum. Each of the through-holes 104c had a diameter of 8 micrometers.

Comparative Example 7

In the comparative examples 7A-7E, an aqueous solution containing both zoospores of Pythium torulosum and zoospores of Pythium helicoides was used in place of the non-phytopathogenic aqueous solution containing zoospores of Pythium torulosum.

Comparative example 7A

In the comparative example 7A, an experiment similar to the inventive example 1A was conducted, except that the aqueous solution contained not only Pythium torulosum but also Pythium helicoides. Each of the through-holes 104c had a diameter of 3 micrometers.

Comparative Example 7B

In the comparative example 7B, an experiment similar to the inventive example 1B was conducted, except that the aqueous solution contained not only Pythium torulosum but also Pythium helicoides. Each of the through-holes 104c had a diameter of 1 micrometer.

Comparative Example 7C

In the comparative example 7C, an experiment similar to the comparative example 1C was conducted, except that the aqueous solution contained not only Pythium torulosum but also Pythium helicoides. Each of the through-holes 104c had a diameter of 0.4 micrometers.

Comparative Example 7D

In the comparative example 7D, an experiment similar to the comparative example 1D was conducted, except that the aqueous solution contained not only Pythium torulosum but also Pythium helicoides. Each of the through-holes 104c had a diameter of 5 micrometers.

Comparative Example 7E

In the comparative example 7E, an experiment similar to the comparative example 1E was conducted, except that the aqueous solution contained not only Pythium torulosum but also Pythium helicoides. Each of the through-holes 104c had a diameter of 8 micrometers.

The following Table 3-Table 9 show the number of the pseudohyphae which penetrated the through-hole 104c in the inventive example 1A—the comparative example 7E.

TABLE 3

|  | Contained Pythium | Diameter of through-hole (micrometer) | Number of the pseudohyphae which penetrated the through-hole 104c |
|---|---|---|---|
| Inventive example 1A | Pythium | 3.0 | 0.0 |
| Inventive example 1B | torulosum | 1.0 | 0.0 |
| Comparative example 1C |  | 0.4 | 0.0 |
| Comparative example 1D |  | 5.0 | 7.0 |
| Comparative example 1E |  | 8.0 | 6.0 |

TABLE 4

|  | Contained Pythium | Diameter of through-hole (micrometer) | Number of the pseudohyphae which penetrated the through-hole 104c |
|---|---|---|---|
| Inventive example 2A | Pythium | 3.0 | 0.0 |
| Inventive example 2B | catenulatum | 1.0 | 0.0 |
| Comparative example 2C |  | 0.4 | 0.0 |
| Comparative example 2D |  | 5.0 | 11.3 |
| Comparative example 2E |  | 8.0 | 5.5 |

TABLE 5

|  | Contained Pythium | Diameter of through-hole (micrometer) | Number of the pseudohyphae which penetrated the through-hole 104c |
|---|---|---|---|
| Inventive example 3A | Pythium | 3.0 | 0.0 |
| Inventive example 3B | inflatum | 1.0 | 0.0 |

TABLE 5-continued

|  | Contained Pythium | Diameter of through-hole (micrometer) | Number of the pseudohyphae which penetrated the through-hole 104c |
|---|---|---|---|
| Comparative example 3C |  | 0.4 | 0.0 |
| Comparative example 3D |  | 5.0 | 7.5 |
| Comparative example 3E |  | 8.0 | 23.5 |

TABLE 6

|  | Contained Pythium | Diameter of through-hole (micrometer) | Number of the pseudohyphae which penetrated the through-hole 104c |
|---|---|---|---|
| Comparative example 4A | Pythium | 3.0 | 18.0 |
| Comparative example 4B | helicoides | 1.0 | 11.0 |
| Comparative example 4C |  | 0.4 | 0.0 |
| Comparative example 4D |  | 5.0 | 94.7 |
| Comparative example 4E |  | 8.0 | 59.7 |

TABLE 7

|  | Contained Pythium | Diameter of through-hole (micrometer) | Number of the pseudohyphae which penetrated the through-hole 104c |
|---|---|---|---|
| Comparative example 5A | Pythium | 3.0 | 48.7 |
| Comparative example 5B | myliotaerum | 1.0 | 1.5 |
| Comparative example 5C |  | 0.4 | 0.0 |
| Comparative example 5D |  | 5.0 | 84.0 |
| Comparative example 5E |  | 8.0 | 31.3 |

TABLE 8

|  | Contained Pythium | Diameter of through-hole (micrometer) | Number of the pseudohyphae which penetrated the through-hole 104c |
|---|---|---|---|
| Comparative example 6A | Pythium aphanidermatum | 3.0 | 21.6 |
| Comparative example 6B |  | 1.0 | 11.6 |
| Comparative example 6C |  | 0.4 | 0.0 |
| Comparative example 6D |  | 5.0 | 53.8 |
| Comparative example 6E |  | 8.0 | 17.6 |

TABLE 9

| | Contained Pythium | Diameter of through-hole (micrometer) | Number of the pseudohyphae which penetrated the through-hole 104c |
|---|---|---|---|
| Comparative example 7A | *Pythium* | 3.0 | 23.0 |
| Comparative example 7B | *torulosum* | 1.0 | 16.0 |
| Comparative example 7C | and | 0.4 | 0.0 |
| Comparative example 7D | *Pythium* | 5.0 | 90.3 |
| Comparative example 7E | *helicoides* | 8.0 | 42.0 |

As is clear from Table 3-Table 9, when the through-hole 104c has a diameter of not less than 1 micrometer and not more than 3 micrometers, the phytopathogenic pythium appears on the back surface 104b of the film 104. On the other hand, within this range of diameter, non-phytopathogenic pythium does not appear on the back surface 104b of the film 104. Therefore, the phytopathogenic pythium 202 appears on the back surface 104b selectively in a case where the through-hole 104c has a diameter of not less than 1 micrometer and not more than 3 micrometers. In other words, the phytopathogenic pythium 202 appears outside of the container 100 selectively.

As is clear from Table 3-Table 9, when the through-hole 104c has a diameter of 0.4 micrometers, neither the non-phytopathogenic pythium nor the phytopathogenic pythium appears on the back surface 104b of the film 104.

As is clear from Table 3-Table 9, when the through-hole 104c has a diameter of not less than 5 micrometers, not only the phytopathogenic pythium but also the non-phytopathogenic pythium appears on the back surface 104b of the film 104.

Therefore, if the through-hole 104c has a diameter of not less than 1 micrometer and not more than 3 micrometers, the pseudohyphae of the non-phytopathogenic pythium does not appear on the back surface 104b of the film 104, whereas the pseudohyphae of the phytopathogenic pythium appears on the back surface 104b of the film 104. Using this difference, a skilled person can determine whether or not all of the pythiums contained in the test sample are non-phytopathogenic pythium.

INDUSTRIAL APPLICABILITY

The present invention can be used to determine easily whether or not all of the pythiums contained in a test sample such as agricultural water or soil are non-phytopathogenic.

REFERENTIAL SIGNS LIST

100 First container
　102 Flange
　　104 Film
　　　104a Front surface
　　　104b Back surface
　　　104c Through-hole
200 Test sample
202 Phytopathogenic pythium
　202a Part of Phytopathogenic pythium
300 Second container
　302 Liquid culture medium
　304 Solid culture medium
402 fluorescent agent having oomycete combining ability
500 Light source
600 Microscope

The invention claimed is:

1. A method for determining whether or not all pythiums contained in a test sample are non-phytopathogenic, the method comprising:
   (a) putting the test sample on a front surface of a film comprising a through-hole having a cross-sectional area of not less than 0.785 square micrometers and not more than 7.065 square micrometers;
   (b) leaving the test sample at rest for six hours after the step (a);
   (c) detecting the presence of pseudohyphae on a back surface of the film opposite to the front surface after the step (b); and
   (d) determining that all the pythiums contained in the test sample are non-phytopathogenic, as a result of a detection that pseudohyphae is not found on the back surface of the film in the step (c).

2. The method according to claim 1, wherein
the pythiums contained in the test sample is at least one selected from the group consisting of Pythium torulosum, Pythium catenulatum, and Pythium inflatum.

3. The method according to claim 1, further comprising:
a step of bringing the back surface of the film into contact with a fluorescent agent for dyeing the pythiums between the step (b) and the step (c).

4. The method according to claim 3, further comprising:
a step of turning the test sample into a gel before the back surface of the film is brought into contact with the fluorescent agent for dyeing the pythiums.

5. The method according to claim 1, further comprising:
a step of supplying a culture medium to the test sample prior to the step (b).

6. The method according to claim 5, wherein
the culture medium is a liquid culture medium.

7. The method according to claim 5, wherein
the culture medium is a solid culture medium.

8. The method according to claim 1, wherein
the test sample is left at rest while the back surface of the film is in contact with the culture medium in the step (b).

9. The method according to claim 1, wherein
the film has a thickness of not less than 10 micrometers and not more than 100 micrometers.

10. The method according to claim 1, wherein
the film comprises a plurality of the through-holes.

11. The method according to claim 1, wherein
the test sample is solid.

12. The method according to claim 11, wherein
the solid test sample is at least one selected from the group consisting of soil and a crushed plant.

13. The method according to claim 1, wherein
the test sample is liquid.

14. The method according to claim 13, wherein
the liquid test sample is at least one selected from the group consisting of agricultural water, a liquid used for hydroponic culture, a liquid used for washing a plant, a liquid extracted from a plant, a liquid used for washing an agricultural material, and a liquid used for washing clothing or a shoe.

15. The method according to claim 1, further comprising:
(e) determining that at least one of the pythiums contained in the test sample is phytopathogenic, as a result of the detection that pseudohyphae is found on the back surface of the film in the step (c).

16. The method according to claim 1, wherein the (c) comprises, observing the back surface by a microscope and irradiating the front surface with light.

17. The method according to claim 1, wherein the film is an organic resin.

18. The method according to claim 17, wherein the organic resin is polyethylene terephthalate.

19. The method according to claim 1, wherein the through-hole has a shape of a cylinder.

* * * * *